United States Patent
Cox et al.

(10) Patent No.: US 7,145,165 B2
(45) Date of Patent: Dec. 5, 2006

(54) TUNABLE LASER FLUID SENSOR

(75) Inventors: James A. Cox, New Brighton, MN (US); Barrett E. Cole, Bloomington, MN (US)

(73) Assignee: Honeywell International Inc., Morristown, NJ (US)

( * ) Notice: Subject to any disclaimer, the term of this patent is extended or adjusted under 35 U.S.C. 154(b) by 43 days.

(21) Appl. No.: 10/953,174

(22) Filed: Sep. 28, 2004

(65) Prior Publication Data

US 2005/0040337 A1 Feb. 24, 2005

Related U.S. Application Data

(63) Continuation-in-part of application No. 09/953,506, filed on Sep. 12, 2001, now Pat. No. 6,816,636, and a continuation-in-part of application No. 10/100,298, filed on Mar. 18, 2002.

(51) Int. Cl.
G01N 15/06 (2006.01)
G01N 21/49 (2006.01)
G01N 21/85 (2006.01)

(52) U.S. Cl. .................. 250/573; 356/437; 356/442

(58) Field of Classification Search ........... 250/343, 250/573, 574, 226; 356/436, 437, 438, 439, 356/441, 442
See application file for complete search history.

(56) References Cited

U.S. PATENT DOCUMENTS

| | | | |
|---|---|---|---|
| 4,614,961 A | 9/1986 | Khan et al. | 257/453 |
| 5,022,745 A | 6/1991 | Zayhowski et al. | 359/847 |
| 5,040,895 A | 8/1991 | Laurent et al. | 355/70 |
| 5,146,465 A | 9/1992 | Khan et al. | 372/45 |
| 5,278,435 A | 1/1994 | Van Hove | 257/184 |
| 5,408,319 A | 4/1995 | Halbout et al. | 356/480 |
| 5,418,868 A | 5/1995 | Cohen et al. | 385/16 |
| 5,450,053 A | 9/1995 | Wood | 338/18 |
| 5,528,040 A | 6/1996 | Lehmann | 250/343 |
| 5,550,373 A | 8/1996 | Cole et al. | 250/378.1 |
| 5,629,951 A | 5/1997 | Chang-Hasnain et al. | 372/20 |
| 5,677,538 A | 10/1997 | Moustakas et al. | 250/370.12 |
| 5,679,965 A | 10/1997 | Schetzina | 257/103 |
| 5,739,554 A | 4/1998 | Edmond et al. | 257/103 |
| 5,834,331 A | 11/1998 | Razeghi | 438/40 |
| 5,847,397 A | 12/1998 | Moustakas | 250/370.06 |
| 5,900,650 A | 5/1999 | Nitta | 257/94 |

(Continued)

FOREIGN PATENT DOCUMENTS

DE  3311808  10/1984

(Continued)

OTHER PUBLICATIONS

Chou et al., "Diode-Laser Measurements of He-, Ar-, and N2-Broadened HF Lineshapes in the First Overtone Band," Journal of Molecular Spectroscopy 196, pp. 70-76, 1999.

(Continued)

*Primary Examiner*—Thanh X. Luu
*Assistant Examiner*—Stephen Yam
(74) *Attorney, Agent, or Firm*—Kris T. Fredrick

(57) ABSTRACT

A sensitive fluid sensor for detecting fluids and particularly trace fluids. The sensor may be adjustable for detecting fluids of various absorption lines. To effect such adjustment, a tunable laser may be used. The laser may be an edge emitting diode, a VCSEL or other tunable source. The detection apparatus of the sensor may incorporate a sample cell through which a laser light may go through. The sample cell may comprise a tunable ring-down cavity. The ring-down cavity may be a ring laser cavity like that of a ring laser gyroscope. There may be a photo detector proximate to the ring down cavity connected to a processor.

13 Claims, 12 Drawing Sheets

U.S. PATENT DOCUMENTS

| | | | | |
|---|---|---|---|---|
| 5,909,280 | A | 6/1999 | Zavracky | 356/454 |
| 5,915,051 | A | 6/1999 | Damask et al. | 385/16 |
| 5,933,565 | A | 8/1999 | Diebold | 385/147 |
| 6,080,988 | A | 6/2000 | Ishizuya et al. | 250/338.1 |
| 6,091,504 | A * | 7/2000 | Walker et al. | 356/437 |
| 6,115,122 | A | 9/2000 | Bao et al. | 356/480 |
| 6,122,416 | A | 9/2000 | Ooba et al. | 385/16 |
| 6,147,756 | A | 11/2000 | Zavracky et al. | 356/519 |
| 6,208,798 | B1 | 3/2001 | Morozov et al. | 385/140 |
| 6,287,940 | B1 | 9/2001 | Cole et al. | 438/455 |
| 6,295,130 | B1 | 9/2001 | Sun et al. | 356/454 |
| 6,296,779 | B1 | 10/2001 | Clark et al. | 216/66 |
| 6,324,192 | B1 | 11/2001 | Tayebati | 372/20 |
| 6,438,149 | B1 | 8/2002 | Tayebati et al. | 372/45 |
| 6,452,680 | B1 * | 9/2002 | Paldus et al. | 356/436 |
| 6,483,130 | B1 | 11/2002 | Yang et al. | 257/189 |
| 6,545,739 | B1 | 4/2003 | Matsumoto et al. | 349/198 |
| 6,584,126 | B1 | 6/2003 | Wang et al. | 372/20 |
| 6,590,710 | B1 | 7/2003 | Hara et al. | 359/579 |
| 6,594,059 | B1 | 7/2003 | Flanders | 359/230 |
| 6,658,034 | B1 * | 12/2003 | Garnache et al. | 372/45.013 |
| 2002/0018385 | A1 | 2/2002 | Flanders et al. | 365/215 |
| 2002/0031155 | A1 | 3/2002 | Tayebati et al. | 372/50 |
| 2002/0106160 | A1 | 8/2002 | Cox et al. | 385/49 |
| 2002/0191266 | A1 | 12/2002 | Seeser et al. | 359/246 |
| 2003/0107739 | A1 * | 6/2003 | Lehmann et al. | 356/437 |
| 2003/0189711 | A1 * | 10/2003 | Orr et al. | 356/484 |
| 2005/0206903 | A1 * | 9/2005 | Tan et al. | 356/437 |
| 2005/0254056 | A1 * | 11/2005 | Kachanov et al. | 356/437 |

FOREIGN PATENT DOCUMENTS

| | | |
|---|---|---|
| EP | 0177918 | 4/1986 |
| EP | 0667548 | 8/1995 |
| EP | 1061618 | 12/2000 |
| EP | 1069658 | 1/2001 |
| JP | 03252172 | 11/1991 |
| JP | 05095130 | 4/1993 |
| JP | 07288334 | 10/1995 |
| WO | WO 9326049 | 12/1993 |
| WO | WO 9942875 | 8/1999 |

OTHER PUBLICATIONS

O'Keefe et al., "Cavity ring-down optical spectrometer for absorption measurements using pulsed laser sources," Review of Scientific Instruments, 59, 11 pages, 1988.

Sadeghi et al., "Cavity Ring Down Spectroscopy Applied to Plasma Diagnostics," Proc. Int. Symp. Laser-aided Plasma Diagnostics, 8 pages, Lake Tahoe, CA, Sep. 1999.

Spence et al., "A laser-locked cavity ring-down spectrometer employing an analog detection scheme," Review of Scientific Instruments, vol. 71, No. 2, pp. 347-353, Feb. 2000.

Bernstein et al., "Development of a Miniature Silicon PhotoAcoustic Gas Sensor", Presented at Opto 96, Leipzig, Germany, Sep. 26-29, 1999, 6 pages.

Brown, J. et al., "Visible-Blind UV Digital Camera Based on a 32*32 Array of GAN/AIGAN P—I—N Photodiodes", MRS Internet Journal of Nitride Semiconductor Research, vol. 4S1, Sep. 1999, XP000949328 ISSN: 1092-5783.

Chitica et al., "Monolithic InP-Based Tunable Filter with 10-nm Bandwidth for Optical Data Interconnects in the 1550-nm Band," IEEE Photonics Technology Letters, vol. 11, No. 5, pp. 584-586, May 1999.

Chung et al., "Design and fabrication of 10×10 micro-spatial light modulator array for phase and amplitude modulation," Sensors and Actuators, vol. 78 No. 1, pp. 63-70, Jan. 1999.

Cole et al., "Microscopic Spectroscopy of Optical MEMS Devices," Topic 2 (Materials and Technology), Honeywell Laboratories, 2 page abstract, submitted on or around Dec. 11, 2000.

Ferber et al., "A Miniature Silicon Photoacoustic Detector for Gas Monitoring Applications", presented at the MTEX 2001. International Conference on Sensors and Transducers, Birmingham, UK, Feb. 14, 2001, 7 pages.

Jerman et al., "A miniature Fabry-Perot interferometer with a corrugated silicon diaphragm support," Sensors and Actuators, vol. !29, No. 2, pp. 151-158, Nov. 1991.

Schweber, "An Old Communications Problem Reoccurs in Optical-Communication-System Design—How it Works: Making the Laser Diode Tunable", EDN, Sep. 28, 2000, pp. 44-48, (www.ednmag.com).

Sze. "Physics of Semiconductor Devices." pp. 763-765, John Wiley & Sons, N.Y., 1982.

Tayebati et al., "Microelectromechanical tunable filter with stable half symmetric cavity," Electronics Letters, IEE Stevanage, GB, vol. 34, No. 20, pp. 1967-1968, Oct. 1998.

Tayebati et. al., "Widely Tunable Fabry-Perot Filters using High Index-contrast DBRs," Design and Manufacturing of WDM Devices, Dallas, Texas, Nov. 4-5, 1997, SPIE vol. 3234, pp. 206-218, 1998.

Yang et al., "Back-Illuminated GAN/AIGAN Heterojunction Photodiodes With High Quantum Efficiency and Low Noise," Applied Physics Letters, vol. 73, No. 8, Aug. 24, 1998, pp. 1086-1088, XP000777678.

* cited by examiner

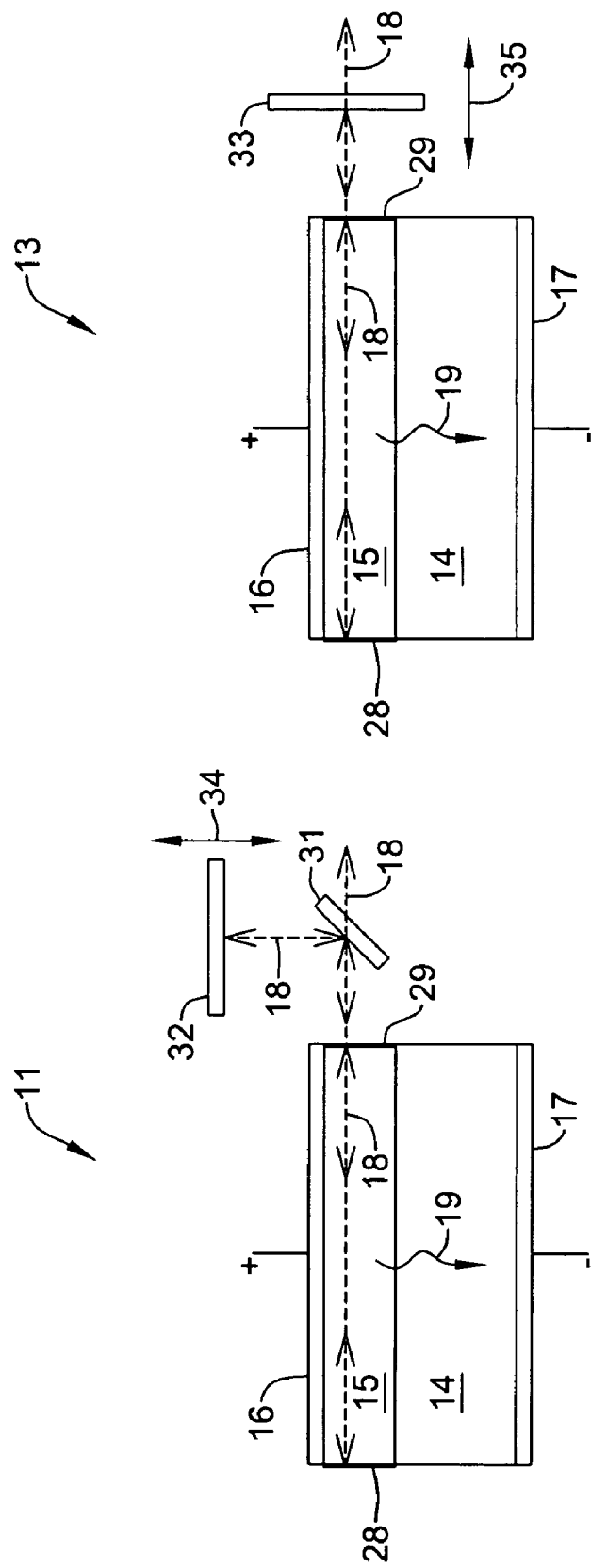

| Bond | Stretching Force Const* | Freq. (cm$^{-1}$) |
|---|---|---|
| =C-H | 5.85 | 3300 |
| =C-H | 5.1 | 3020 |
| >C-H | 4.79 | 2960 |
| -O-H | 7.66 | 3680 |
| >N-H | 6.35 | 3350 |
| -C=N | 17.73 | 2100 |
| >C=O | 12.1 | 1700 |

| Bond | Stretching Force Const* | Freq. (cm$^{-1}$) |
|---|---|---|
| -C=C- | 15.59 | 2050 |
| >C=C< | 9.6 | 1650 |
| >C-C< | 4.50 | 900 |
| >C-F | 5.96 | 1100 |
| >C-Cl | 3.64 | 650 |
| >C-Br | 3.13 | 560 |
| >C-I | 2.65 | 500 |

| Bond | Bending Force Const* | Freq. (cm$^{-1}$) |
|---|---|---|
| =C-H | $0.21 r_b^2$ | 700 |
| =C<H,H | $0.51 r_b^2$ | 1100 |
| -C<H,H | $0.55 r_b^2$ | 1000 |
| >C<H,H | $0.30 r_b^2$ | 1450 |
| C=C-C | $0.155 r_b^2$ | 300 |

* ($\times 10^5$ dyne/cm$^2$)

Figure 2

| T(K) | res | Gth | OPL$_{topmir}$ | OPL$_{diel}$($\lambda$) |
|---|---|---|---|---|
| . | | | | |
| . | | | | |
| . | | | | |
| 375 | 1299.6 | 744.1 | 85.975 | 81.749 |
| | 1300.7 | 746.9 | 86.061 | 81.836 |
| | 1301.8 | 753.5 | 86.148 | 81.922 |
| | 1302.9 | 762.7 | 86.235 | 82.009 |
| 400 | 1304.0 | 775.0 | 86.321 | 82.096 |

TUNABLE LASER FLUID SENSOR

This invention is a continuation-in-part of U.S. patent application Ser. No. 09/953,506, filed Sep. 12, 2001, now U.S. Pat. No. 6,816,636 by B. Cole et al., and entitled "Tunable Optical Filter", which is incorporated herein by reference. This invention is also a continuation-in-part of U.S. patent application Ser. No. 10/100,298, filed Mar. 18, 2002, by B. Cole et al., and entitled "Spectrally Tunable Detector", which is incorporated herein by reference.

BACKGROUND

The invention pertains to fluid detection, and particularly to laser detection of fluids. More particularly, the invention pertains to detection of trace fluids.

There appears to be a need for a compact sensor that can detect and identify fluids with very high sensitivity, for applications related to security, industrial process control, and air quality control.

SUMMARY

The invention may be a very sensitive compact fluid sensor using a tunable laser and a cavity.

BRIEF DESCRIPTION OF THE DRAWING

FIGS. 1b and 1c show illustrative examples of tunable edge emitting diodes;

FIG. 2 is a table of characteristic frequencies of common bond groups;

FIG. 12 is table of temperatures and various parameters of the VCSEL.

DESCRIPTION

Figure 1A:
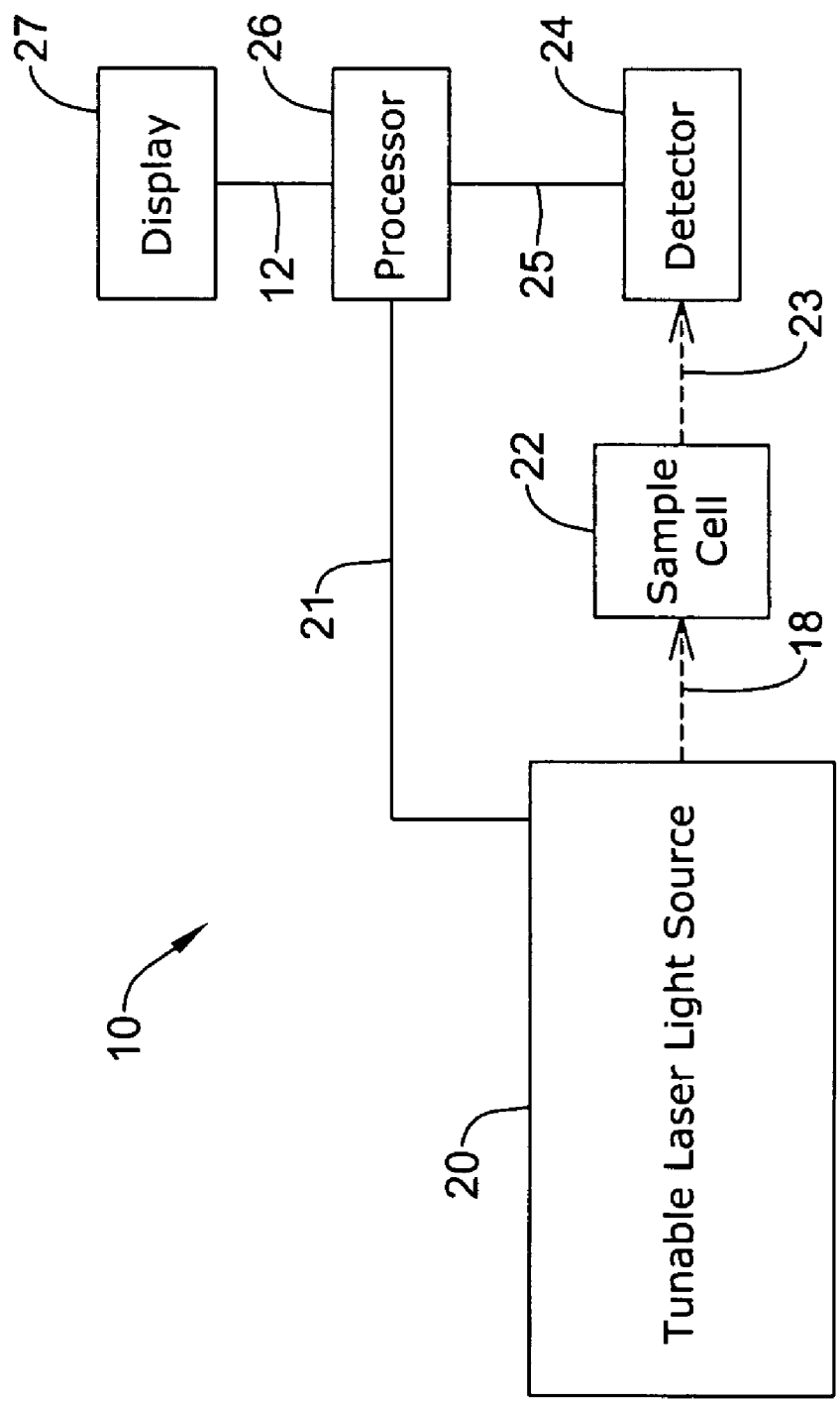
FIG. 1a is a basic sample cell configuration with a tunable laser.

FIG. 1a reveals a configuration 10 of a cell 22 with a tunable laser light source 20. The tunable laser 20 may incorporate a diode laser, a vertical cavity surface emitting laser (VCSEL), or other type of tunable laser. The tunable laser 20 may have its wavelength varied for detecting and analyzing various fluids. The wavelength may be pre-programmed or varied real-time during detection and analysis.

The present invention may include a tunable laser or other tunable source coupled with a device to directly detect molecular absorption at specific wavelengths addressable with the tunable laser. One way is to tune the lasing wavelength of a laser diode, such as, an edge emitting diode or VCSEL. A way to tune the lasing wavelength is to use a MEMS-actuated etalon having a mirror of a laser resonant cavity, and a thermally-tuned microbridge mirror in a Fabry-Perot cavity. The tunable laser may be coupled into one of two detection cells capable of directly sensing absorption in the gas of interest. This device may be an opto-acoustic cell or a ring-down cavity. The opto-acoustic cell may be used for lower cost and lower performance applications. The ring-down cavity may be implemented into a cavity ring-down spectrometer. The ring-down spectrometer may be used in applications requiring the highest sensitivity. The tunable laser may be needed for identification of specific molecular species of interest. The ring-down cavity may be implemented with methods and technology developed for ring laser gyros. The ring-down cavity may be a ring laser cavity produced for ring laser gyroscopes.

The detection may be of a fluid, i.e., a gas or liquid. The description may, for illustrative purposes, deal with gas detection and discrimination. The sensitivity of the sensor may be application dependent. Significant targets of the sensor may be explosives and chembio agents. The sensitivity of the sensor may range from ppb to ppt levels. The size of the sensor may be only about one to three cubic inches, i.e., about 15–50 $cm^3$.

The spectral absorption of molecular vibration/rotation modes may be expressed as A=SDL, where A is absorbance, S is a molecular cross-section, D is molecular density and L is path length. $S_{peak}(\lambda)$ may vary by 2–3 orders of magnitude in the waveband of 1 to 8 microns. $S_{peak}(\lambda)$ may be the largest for the fundamental vibration/rotation modes (generally in the 3 to 8 micron band). $S_{peak}(\lambda)$ may be the smallest for harmonics (generally in the 1 to 2 micron band).

Examples of $S_{peak}(\lambda)$ may include:

$CO_2$(4.3 μm)~1×10$^{-18}$($cm^2$/mol)$cm^{-1}$(max.>1–8 μm)

$H_2O$ (1.4 μm)~2×10$^{-20}$($cm^2$/mol)$cm^{-1}$(max.=3×10$^{19}$ at ~5.9 μm)

$NH_3$(1.53 μm)~2×10$^{-21}$($cm^2$/mol)$cm^{-1}$(max.=2.2×10$^-$20 at ~3.0 μm)

The spectral signature (S(λ)) may indicate a species discrimination.

The threshold limit values (TLVs) may be important to know since one objective is detection of lethal chemicals. The following are examples of such chemicals and their threshold limits. Blood agents may include arsine (Ar) ($ArH_3$), which may be a blood type agent having a TLV of about 50ppb. Cyanogen chloride (CClN) may be a blood type agent having a TLV of about 300 ppb. Hydrogen cyanide (CHH) may be a blood type agent having a TLV of about 4700 ppb. Chloropicrin (PS) ($CCl_3NO_2$) may be a choking type of agent having a TLV of about 100 ppb. Mustard (HD) ($C_4H_8Cl_2S$) may be a blister type of agent having a TLV of about 0.5 ppb. Methyl phosphorothioate (VX) ($C_{11}H_{26}NO_2PS$) may be a nerve type of agent having a TLV of about 0.8 ppt. Isopropyl methyl phosphonofluoridate (GB, sarin) ($C_4H_{10}FO_2P$) may be a nerve type of agent having a TLV of 16 ppt. Ethyl N, N-dimethyl phosphoramidocyanidate (GA, tabun) ($C_5H_{11}N_2O_2P$) may be a nerve type of agent having a TLV of abut 14 ppt. Pinacoly methyl phosphonofluoridate (GD, soman) ($C_7H_{16}Fo_2P$) may be a nerve type agent having a TLV of about 3 ppt. These are the kinds of chemicals that the present sensor may detect and identify. These are examples of chemicals of concern along with these TLV levels that the present sensor may detect. TLV may represent the maximum airborne concentrations of substances that in general may be exposed day after day during normal workers' hours with no adverse effect.

A tunable laser module 20, as shown in FIG. 1a, may be used to discriminate molecular species. Typically, common bond groups may have characteristic absorption regions. However, each molecule may have a unique vibrational spectrum. The characteristic absorption regional and the vibrational spectrum information may be useful for identifying species of substances. FIG. 2 has a table of approximate characteristic frequencies of common bond groups.

Figures 3, 4:
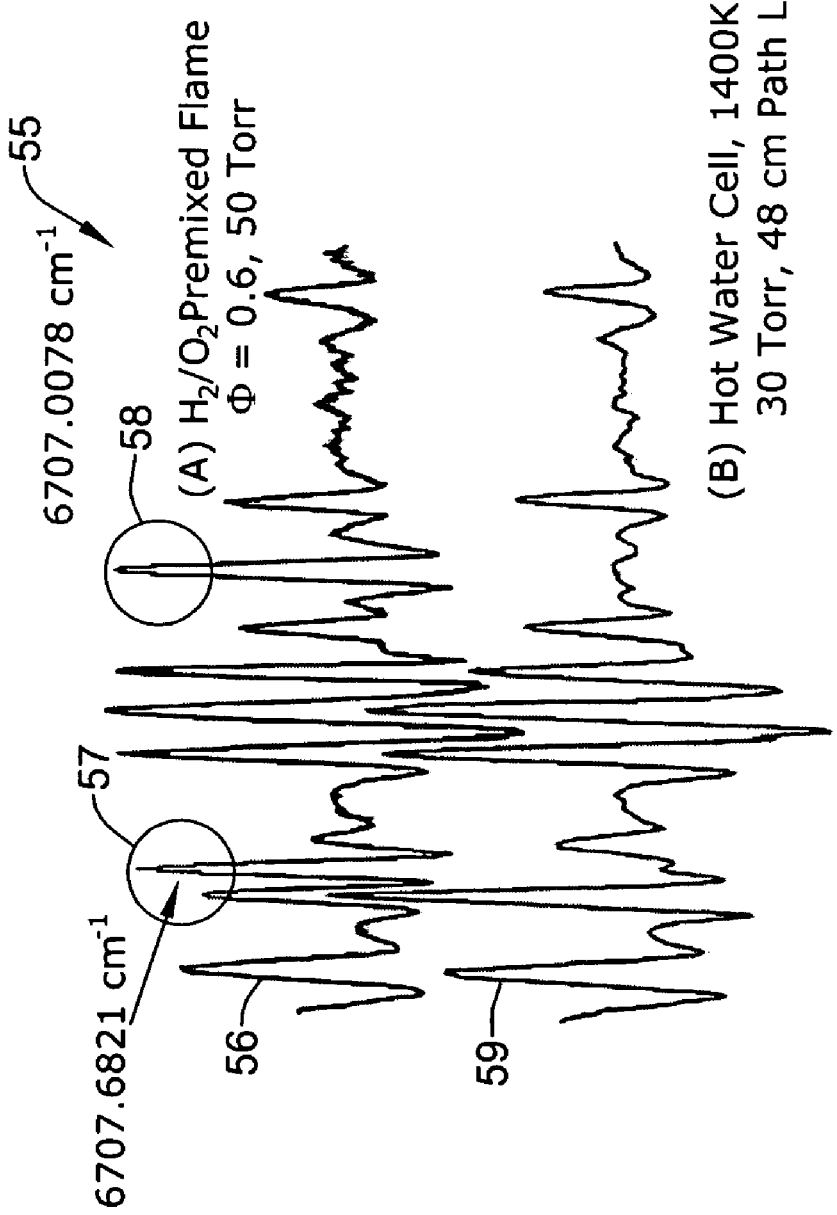
FIG. 3 is a display of results of detection and analysis of a fluid.
FIG. 4 is a table of originating wavelengths versus a delta wavelength.

In FIG. 1a, a laser 20 may emanate light 18 of a particular wavelength. From laser 20, light 18 may propagate through sample cell 22. A resultant light 23 may emanate from sample cell 23 to detector 24. Electrical signals 25 from detector 24 to a controller 26 may be the electrical equivalent of light 23. Controller 26 may process the signals 25 from detector 24 and send resultant signals 12 to display 27. As an illustrative example, display 27 may exhibit a graphical picture as shown in FIG. 3. Also, processor 26, via signals 21 to source 20, may tune light source 20 to an absorption line of the fluid (e.g., gas) in the sample cell 22. Sample cell 22 may incorporate a device likewise tuned to the absorption line, such that the light in the device has an appropriate phase relationship with the light from the light source. Such tuned combination improves the sensitivity of the device 10 in an exceptional manner.

FIGS. 1b and 1c reveal examples of edge emitting laser 11 and 13 respectively. These lasers may be used as the source 20 of configuration 10 of FIG. 1a. Lasers 11 and 13 may have some similarity of structure such as a substrate 14 with a cavity 15 formed on the substrate 14. Cavity 15 may have a mirror 28 formed at one end and a mirror 29 formed at the other end. In cavity 15 may be a quantum well structure. Formed on cavity 15 may be a metal layer 16 formed on the surface of cavity 15 opposite of the surface adjacent to the substrate 14. On the other surface or bottom of the substrate may be a metal layer 17 formed. Layer 16 may be an electrode for a positive potential of an electrical connection and layer 17 may be an electrode for a negative potential of the electrical connection. Applying these potentials to the electrodes may result in a current 19 flowing from layer 16 through cavity 15 and substrate 14 to layer 17. This may result in light being 18 generated in resonate between the mirrors 28 and 29 of cavity 15 with a portion of light 18 being emitted out of one or both ends of the cavity 15. In lasers 11 and 13, mirror 28 is very highly reflective and mirror 29 is only slightly less reflective than mirror 29, so as to let light 18 be emitted out of the cavity 15 through mirror 29. Mirror 29 may have an anti-reflective coating.

The differences between lasers 11 and 13 appear between their tuning structures. In FIG. 1b, some of light 18 may be reflected by a splitter 31 to an adjustable mirror 32 or etalon. Light 18 reflected back by mirror 32 may be reflected back at least partially into the cavity 15 by splitter 31. The distance of travel of light 18 being reflected by mirror 31 may affect the resonant frequency of the cavity 15 and thus the wavelength of the light 18 emanating from the cavity 15 and passing through the splitter 31 as an output of laser 11. Thus, the wavelength of the output light of laser 11 may be changed or tuning by a movement of mirror 32 in directions 34 towards or from splitter 31.

The tuning structure of laser 13 in FIG. 1c may have a mirror 33 situated proximate and parallel to the mirror 29 at the end of cavity 15. Light 18 may emanate from cavity 15 through mirror 29 towards a partially transmissive mirror 33. Some of the light 18 may be reflected back from mirror 33 into cavity 15. The distance of mirror 33 from cavity 15 at mirror 29 may affect the resonant frequency of the cavity and thus the wavelength of the light 18 emanating from laser 13 through mirror 33 from cavity 15. Thus, the wavelength of the output light of laser 13 may be changed or tuned by a movement of mirror 33 in directions 35 towards or from mirror 29 of cavity 31.

FIG. 3 shows the results of an observation 55 from display 27 which shows an illustrative view of the detector 24 results of light 23 exiting from sample cell 22. Waveform 56 is that of a $H_2/O_2$ premixed flame where $\Phi=0.6$ under a pressure of 50 Torr. Two peaks of interest are peak 57 at 6707.6821 cm$^{-1}$ and peak 58 at 6707.0078 cm$^{-1}$. Waveform 59 is that of a hot water cell at 1400° K., a pressure of 30 Torr and a 48 cm path length.

FIG. 4 is a table of the wavelength of an emanating light and the resultant delta of wavelength, at various wavelengths of the originating light.

Figure 5:
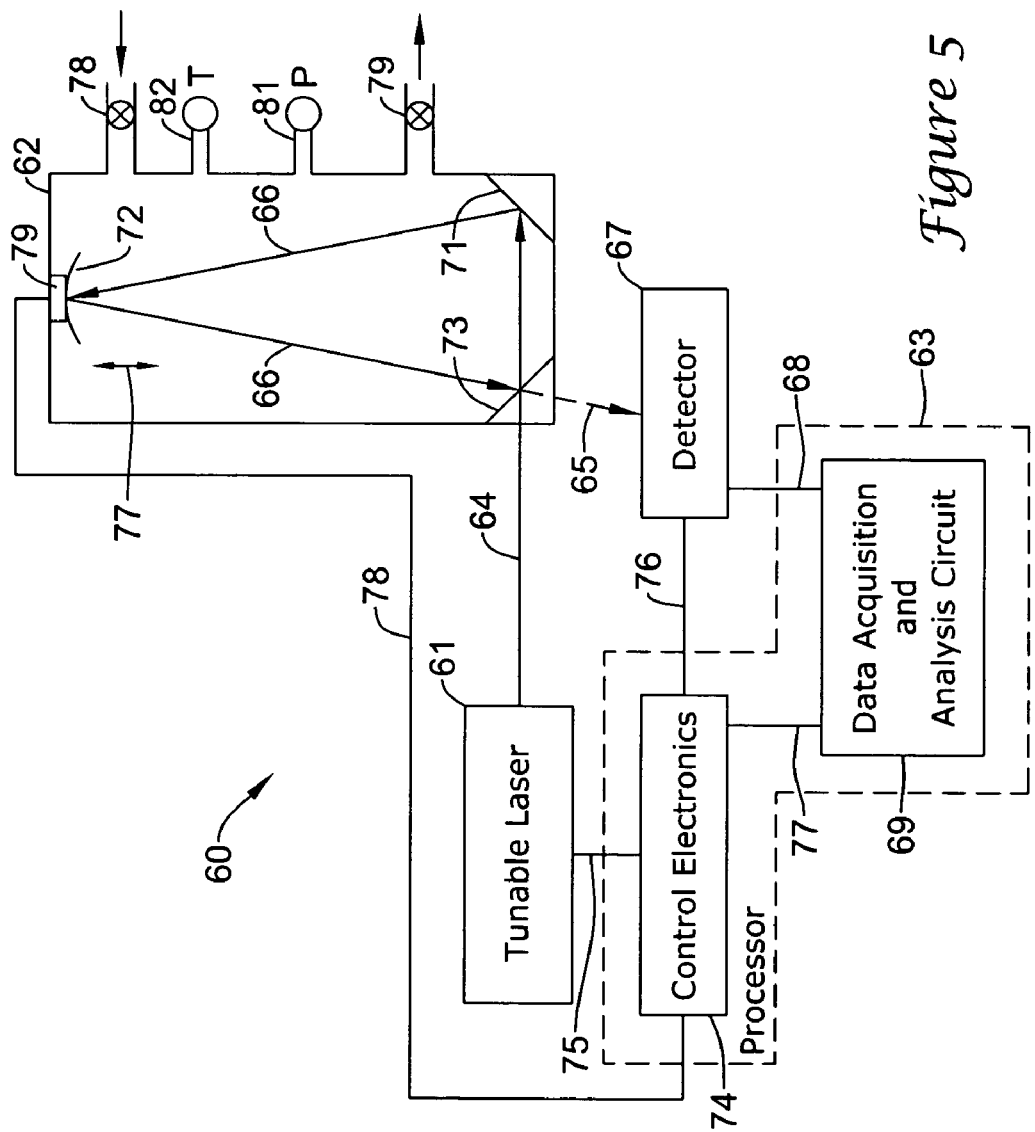
FIG. 5 is a cavity-ring down spectroscophy cell with a wavelength-tunable light source.

As shown in FIG. 5, a tunable laser 61 may be coupled to a three mirror optical ring-down cavity 62. One of the mirrors, e.g., mirror 72, may have a slight and high radius curvature to improve stability so that a light beam 66 does not walk off the cavity. Cavity 62 may be a ring laser cavity or a ring laser gyroscope cavity, though not functionally used as a gyro. Cavity 62 instead may have two mirrors, four mirrors, or any other number of mirrors providing a light path selected from various possible routes for light in the cavity. There may be an analog detection circuit 63 to extract the ring-down rate from an exponentially decaying ring-down waveform. A technique may be used to measure trace concentrations of gases in the near infrared region using a continuous wave excitation 64 of a cavity-ring down spectroscopy cell or cavity 62. (CW-CRDS). Cavity ring-down spectroscopy may be an absorption technique in which light 64 is coupled into a high finesse optical resonator 62. The cavity 62 may be tuned to the absorption line of the gas in the cavity being sensed and quantitatively measured. Cavity 62 may be tuned such that light 66 is in phase with the incoming light 64. This tuning, such as adjusting the path length of light 66, may be applicable to other kinds of cavities, such as those with two mirrors, four mirrors, and the like. Tuning the cavity with mirror 72 adjustment 77 with an actuator 79 may be one way of adjustment. Similarly, a light source 61 may have an output wavelength tuned to the absorption line of the gas in the cavity. By monitoring the decay rate of the light 66 inside the cavity with detection circuit 63 which includes a detector 67, one may determine a concentration of a particular gas in the cavity 62. The near infrared light 65 detected may contain vibrational overtone transitions and forbidden electronic transitions of various atmospheric species of gas. System 60 may obey Beer's law and provide a highly accurate concentration determination. The effective path length of the light 66 in the cavity may be about a hundred times larger than the physical size of the cell 62 due to highly reflective dielectric mirrors 71, 72 and 73. Mirror 72 may have an adjustment 77 for tuning the path length of cell 62 for light 66.

There may be fast trace gas impurity measurements of critical molecules such as $H_2O$, CO, $NH_3$, HF, HCl, $CH_4$ and $C_2H_2$. Such measurements may be made in seconds. Trace moisture concentration may be measured at levels from parts per billion (ppb) to parts per trillion (ppt).

Tunnel laser 61 may send a continuous wave (or possibly pulsed) light signal to cell 62. Signal 64 may be regarded as a signal 66 that is reflected around in cell 62 from mirror 71, to mirror 72, to mirror 73, to mirror 71 and so on until the signal 66 diminishes. Some light 65 may leave cell 62 and impinge detector 67. Detector 67 may convert light signal 65 to an electrical signal 68 that goes to a data acquisition and analysis unit 69. Control electronics 74 may send control signals 75, 76 and 77 to tunable laser 61, detector 65 and data acquisition and analysis unit 69, respectively. Also, a control signal 78 may be sent to a moveable support 79 of mirror 72 to provide tenability of the path for light 66. Support 79 may be a piezoelectric transducer to allow tuning and modulation of the path length of cell 62.

One may detect a certain fluid using a laser tuned on a transition band, near a particular frequency. Using system 62, one may be able to measure the concentration of the fluid in some medium. The certain fluid and associated medium may enter a port 78 and exit a port 79. Port 81 may be for a connection to a pump. Port 82 may be used for a gauge.

The system 60 may provide for an intrinsic measure of absorption. The CRDS sensitivity may equal $$(\Delta t/t)(L_{opt/Lcav})(1/F_{acq})^{1/2}$$

Another relationship may be:

$$L_{opt} \sim L_{cav}/[n_{mirror}(1-R)] \sim 10^4 L_{cav}$$

Typical sensitivity may be at about $10^{-6}$ to $10^{-10}$ cm$^{-1}$ for multimode light and about $10^{-9}$ to $10^{-12}$ cm$^{-1}$ for single mode light.

The system 62 may be built on the strengths of a MEMS etalon, ring laser gyro technology and VCSELs.

Figure 6:
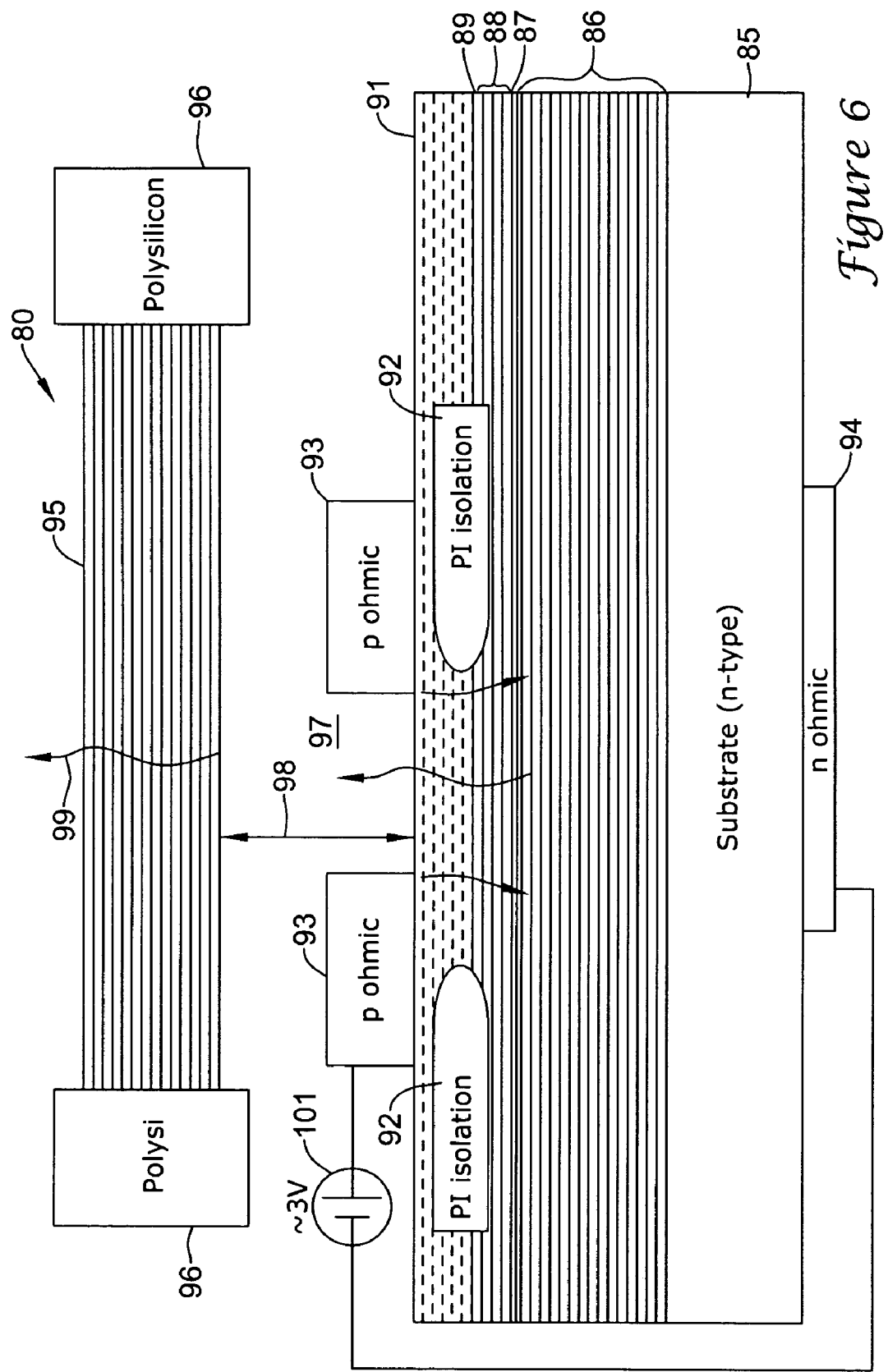
FIG. 6 is a diagram of an adjustable wavelength vertical cavity surface emitting laser (VCSEL)

FIG. 6 shows a tunable VCSEL 80. It may have an n type GaAs substrate. On substrate 85, may be a bottom distributed Bragg reflector (DBR) mirror 86. Mirror 86 may be an n type having 35.5 periods of AlAs/GaAs graded layers. On mirror 86, may be an n type spacer 87. On active region 88 may be situated on n spacer 87. Active region 88 may have three GaInAsN/GaAs quantum wells with barriers between them. A p type spacer 89 may be situated on active region 88. On active region 88 may be a layer 91 of p type GaAs for current spreading. Layer 91 may have a thickness of about 1200 nm. There may be a proton implanted isolation 92 for current confinement. Isolation 92 may be implanted in layer 91 and possibly in a portion of p type spacer 89. Situated on layer 91 may be a p type ohmic contact 93. On the bottom of substrate 85 may be an n type ohmic contact 94.

Situated above layer 91 and contact 93 may be a p type distributed Bragg reflector mirror 95. Mirror 95 may have 4.5 periods of TiO$_2$/SiO$_2$ layers. Mirror 95 may be supported by a polysilicon structure 96 over layer 91 with an air gap 97 between mirror 95 and layer 91. The air gap 97 may have a distance or linear dimension 98 of (2 m+1)/4. The cavity formed by mirrors 86 and 95 may be changed by adjusting mirror 95 relative to mirror 86. This adjustment of distance 98 may affect the wavelength of the light 99 output from VCSEL 80. Mirror 95 may be effectively an etalon of VCSEL 80.

To operate VCSEL 80, a voltage from a source 101 may have a positive polarity applied to the p ohmic contact 93 and the other polarity applied to n ohmic contact 94. The voltage source 101 may be about three volts. The connection of source 101 to VCSEL 80 may cause a current to flow downwards from contact 93 through layer 91 with isolation 92, and through other components of the VCSEL to contact 94 consequently, light 99 may be emitted upwards from active region 88 through spacer 89, layer 91, and air gap 97. Some of the light 99 may be reflected within the cavity between mirrors 86 and 95.

Figure 7:
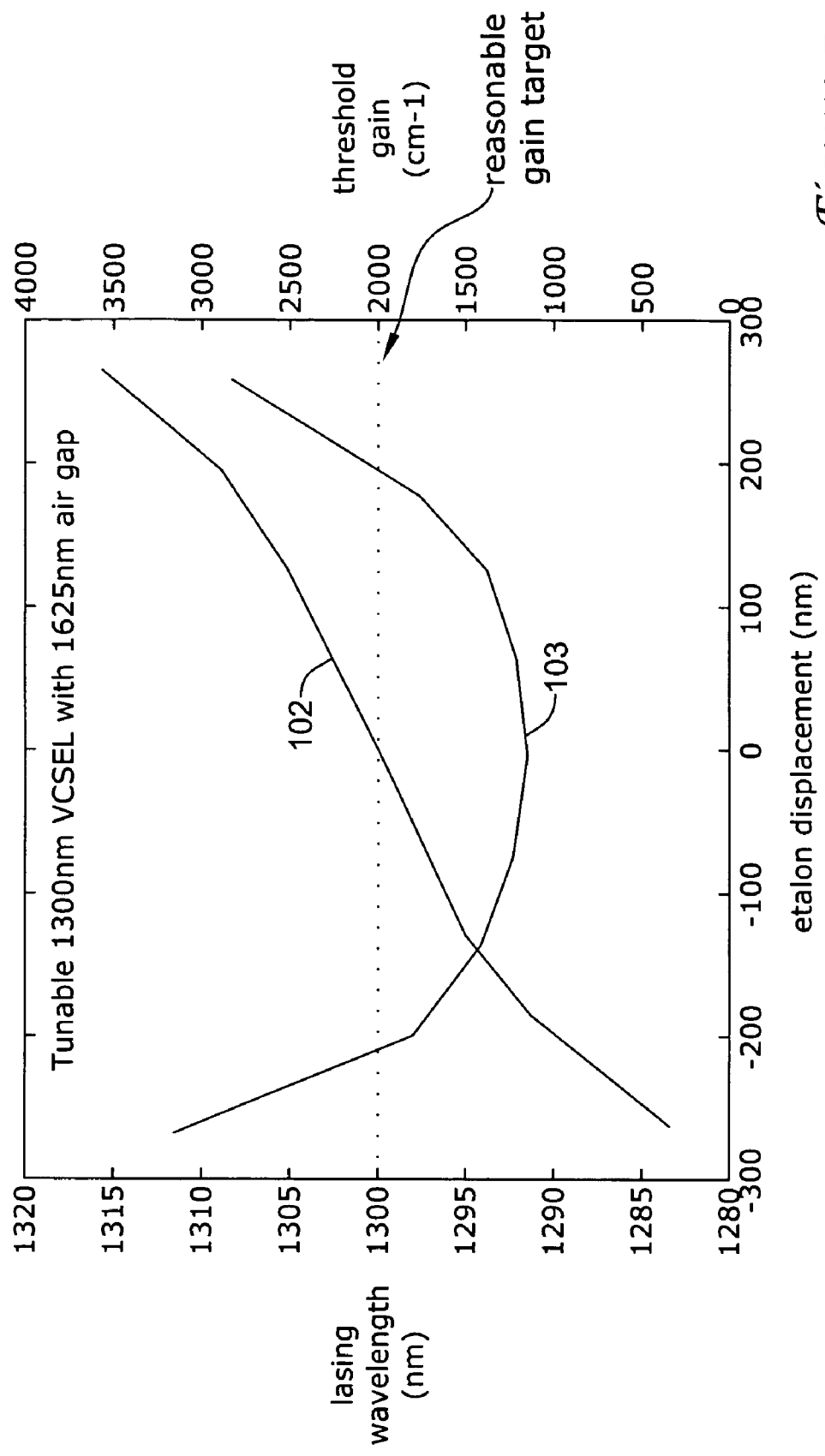
FIG. 7 is a chart showing lasing wavelength and threshold gain versus etalon displacement of VCSEL.

FIG. 7 is a graph showing tunability and threshold gain versus etalon displacement 98 change from the displacement setting for 1300 nm of VCSEL 80 with a 1625 nm air gap. Curve 102 shows the lasing wavelength versus etalon displacement. Curve 103 shows the threshold gain (cm$^{-1}$) versus etalon displacement. The displacement may be limited to ±200 nm.

A reasonable gain target may be 2000 cm$^{-1}$. There is about a 20 nm tuning range from about 1290 nm to 1310 nm. The tuning range may be limited by the bottom mirror 86 $\Delta$n. The tuning efficiency may be about 5 percent.

Figure 8:
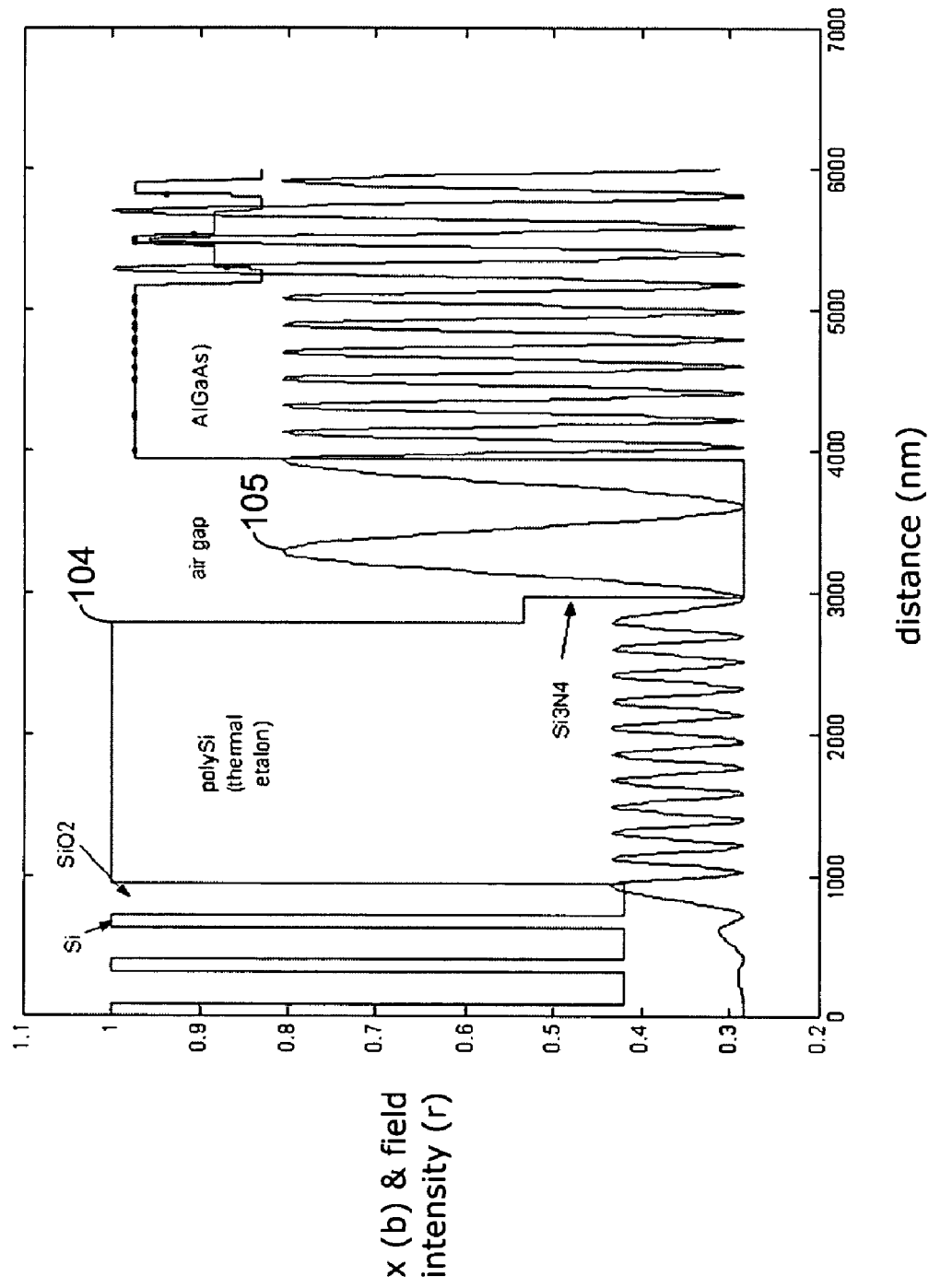
FIG. 8 shows field intensity versus distance in the structure of the VCSEL.
Figure 9:
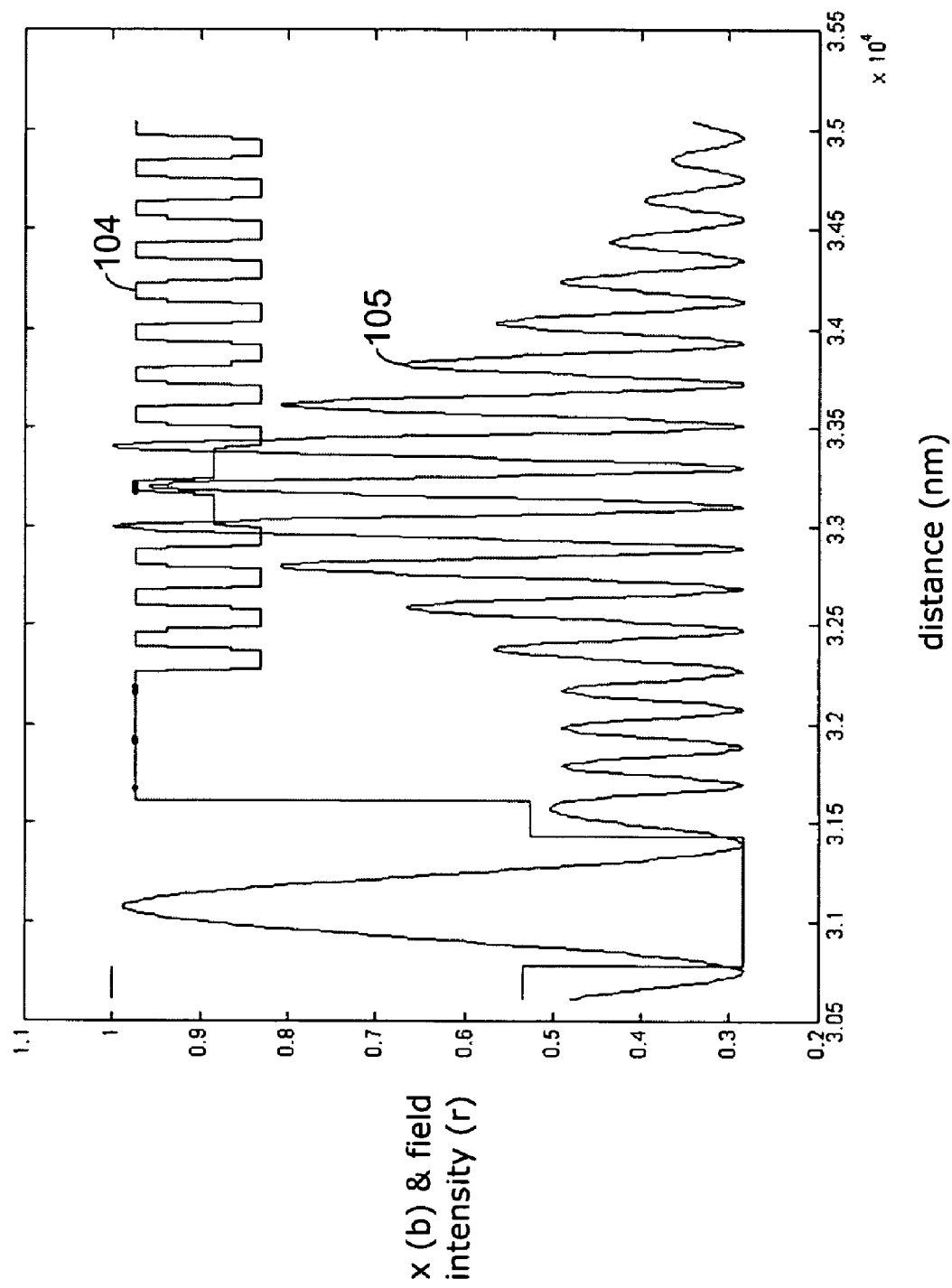
FIG. 9 is a continuation of the field intensity versus distance in the VCSEL.

FIG. 8 shows the side profile of material with x(b) and field intensity (r) versus distance nm through the VCSEL 80. Curve 104 shows the material profile through the VCSEL 80 with the Si and SiO$_2$ layers, the polysilicon (thermal etalon), the Si$_3$N$_4$, the air gap, and the AlGaAs structure. Curve 105 shows the field intensity relative to distance into the structure of VCSEL 80. FIG. 9 is a contamination of x(b) and field intensity versus distance into VCSEL 80 structure, and continues at about the air gap portion of FIG. 8, as indicated by the distance axis.

Figure 10:
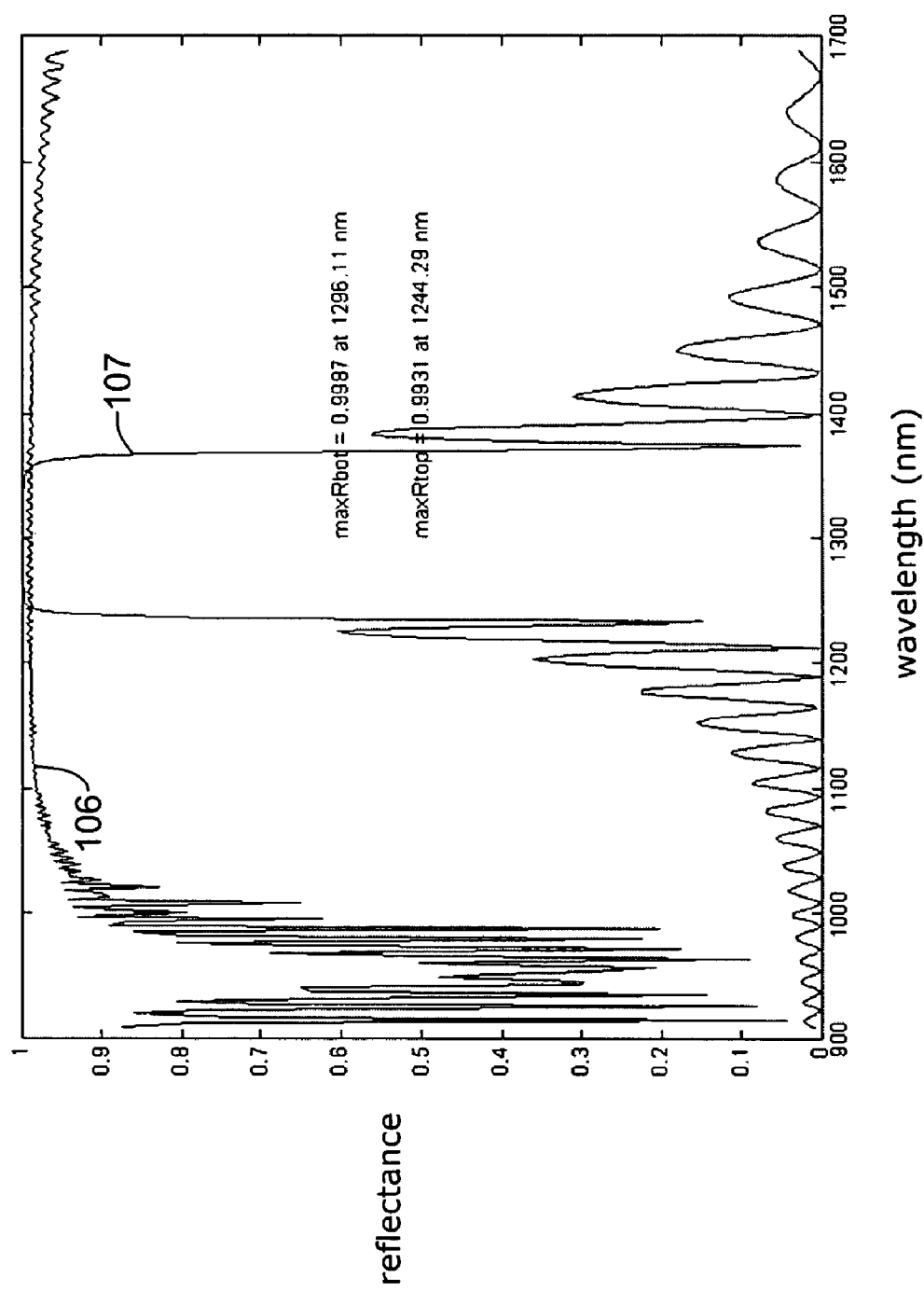
FIG. 10 shows the reflectivity of the VCSEL mirrors versus wavelength.

FIG. 10 reveals the reflectance versus wavelength curves 106 and 107 for the top mirror and the bottom mirror, respectively, of VCSEL 80. The maximum reflectance for the top mirror is about 0.9931 at 1244.29 nm wavelength. The maximum reflectance for the bottom mirror is about 0.9987 at 1296.11 nm wavelength.

Figure 11:
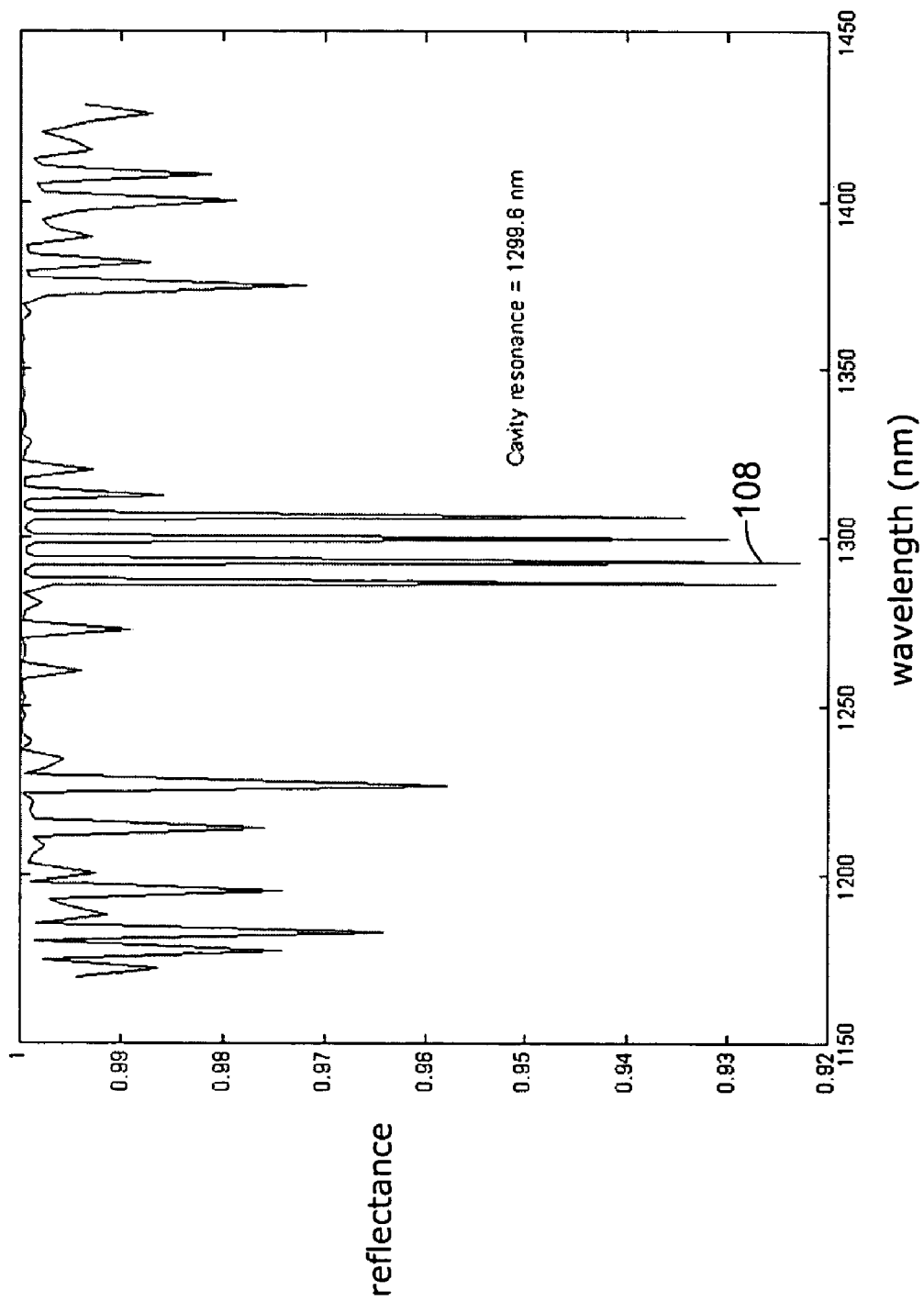
FIG. 11 reveals the reflectance of the VCSEL resonant cavity versus wavelength.

FIG. 11 shows reflectance versus wavelength. Curve 108 reveals the resonant cavity reflectance for the VCSEL 80, in the aperture. The cavity resonance may be determined to be about 1299.6 nm.

FIG. 12 shows a table with temperature in Kelvin (K) degrees, and data about the cavity resonance, the Gth, $OPL_{topmirror}$ and $OPL_{dielectric}$. The OPL of the Si spacer may increase about 0.1 $\lambda$ per 25° K., but its effectiveness in changing the Fabry-Perot (FP) cavity is reduced by the three AlGaAs periods immediately on the top of the active region 88. These periods were added to reduce the effective cavity length and thus spread the FSR.

Although the invention has been described with respect to at least on illustrative embodiment, many variations and modifications will become apparent to those skilled in the art upon reading the present specification. It is therefore the intention that the appended claims be interpreted as broadly as possible in view of the prior art to include all such variations and modifications.

What is claimed is:

1. A fluid sensor comprising:
   a tunable light source;
   a cavity positioned to receive light from the tunable light source; and
   a detector positioned to receive light from the cavity; and
   wherein:
   the tunable light source is an edge emitting diode; and
   the edge emitting diode comprises:
   a substrate;
   a layer, having a laser cavity with reflective surfaces situated at the edges of the laser cavity, situated on the substrate; and
   a moveable mirror proximate to one edge for tuning the laser cavity.

2. The sensor of claim 1, wherein the moveable mirror may be adjusted to tune the laser cavity to a particular wavelength.

3. A fluid sensor comprising:
   a tunable light source;

a ring down cavity positioned to receive light from the tunable light source; and
a detector positioned to receive light from the ring down cavity; and
wherein:
the tunable light source is a VCSEL; and
the VCSEL comprises:
a substrate;
a first mirror situated on the substrate;
an active area situated on the first mirror; and
a second mirror situated at a variable distance from the first mirror.

4. The sensor of claim 3, wherein the variable distance may be adjusted to tune the VCSEL to a particular wavelength.

5. The sensor of claim 4, wherein the wavelength may be adjusted to determine the kind of fluid in the ring down cavity.

6. The sensor of claim 3, wherein the VCSEL further comprises:
a current spreading layer on the active region; and
an adjustable gap between the second mirror and the current spreading layer.

7. The sensor of claim 6, wherein the VCSEL further comprises:
a first spacer situated between the first mirror and the active region; and
a second spacer situated between the active region and the current spreading layer.

8. The sensor of claim 7, wherein the VCSEL further comprises a current confinement region situated at least partially in the current spreading layer.

9. The sensor of claim 8, wherein the VCSEL has an infrared bandwidth.

10. A fluid sensor comprising:
a tunable light source;
a ring down cavity positioned to receive light from the tunable light source; and
a detector positioned to receive light from the ring down cavity; and
wherein:
the ring down cavity comprises:
a containing structure;
a first mirror positioned in the containing structure to receive light from the tunable light source; and
at least another mirror positioned in the containing structure to receive light reflected by the first mirror arid reflect it back to the first mirror and vice versa for a plurality of times;
the at least another mirror is moveable to adjust the wavelength of the containing structure;
the light source is tuned to an absorption line of a fluid in the containing structure;
the detector is proximate to the at least another mirror to detect light reflected in the containing structure;
the ring down cavity is a ring laser cavity;
the containing structure is tuned to an absorption line of the fluid in the containing structure; and
the tunable light source is an edge emitting diode.

11. The sensor of claim 10, wherein the edge emitting diode comprises:
a substrate;
a layer, having a laser cavity with reflective surfaces situated at the edges of the cavity, situated on the substrate; and
a moveable mirror proximate to one edge for tuning the laser cavity.

12. The sensor of claim 11, wherein the moveable mirror may be adjusted to tune the laser cavity to a particular wavelength.

13. The sensor of claim 12, wherein the wavelength may be adjusted to determine the kind of fluid in the containing structure.

* * * * *